United States Patent
Beyer

(10) Patent No.: US 10,058,355 B2
(45) Date of Patent: Aug. 28, 2018

(54) ORTHOPEDIC IMPLANT KIT

(71) Applicant: Neo Medical S.A., La Villette (CH)

(72) Inventor: Morten Beyer, Rodkaersbro (DK)

(*) Notice: Subject to any disclaimer, the term of this patent is extended or adjusted under 35 U.S.C. 154(b) by 21 days.

(21) Appl. No.: 14/890,631

(22) PCT Filed: Apr. 24, 2014

(86) PCT No.: PCT/IB2014/060979
§ 371 (c)(1),
(2) Date: Nov. 12, 2015

(87) PCT Pub. No.: WO2014/184694
PCT Pub. Date: Nov. 20, 2014

(65) Prior Publication Data
US 2016/0089186 A1 Mar. 31, 2016

(30) Foreign Application Priority Data

May 13, 2013 (WO) .................. PCT/IB2013/053892

(51) Int. Cl.
*A61B 17/70* (2006.01)
*A61B 17/88* (2006.01)

(52) U.S. Cl.
CPC ...... *A61B 17/7037* (2013.01); *A61B 17/7002* (2013.01); *A61B 17/708* (2013.01); *A61B 17/7032* (2013.01); *A61B 17/7038* (2013.01); *A61B 17/7085* (2013.01); *A61B 17/7086* (2013.01); *A61B 17/7091* (2013.01); *A61B 17/8875* (2013.01)

(58) Field of Classification Search
CPC ............ A61B 17/7035; A61B 17/7037; A61B 17/7038; A61B 17/7046; A61B 17/7074; A61B 17/7076; A61B 17/7077; A61B 17/7079; A61B 17/708; A61B 17/7082; A61B 17/7083; A61B 17/7085; A61B 17/7086; A61B 17/7088; A61B 17/7091
See application file for complete search history.

(56) References Cited

U.S. PATENT DOCUMENTS

| 6,371,968 | B1 * | 4/2002 | Kogasaka | ........ A61B 17/00234 |
| | | | | 600/201 |
| 7,160,300 | B2 * | 1/2007 | Jackson | ............ A61B 17/7011 |
| | | | | 606/273 |

(Continued)

FOREIGN PATENT DOCUMENTS

| CN | 202446242 | 9/2012 |
| CN | 202497225 U | 10/2012 |

(Continued)

OTHER PUBLICATIONS

International Search Report dated Nov. 25, 2014 in International Application No. PCT/IB2014/060979, 5 pages.

(Continued)

*Primary Examiner* — Lynnsy Summitt
(74) *Attorney, Agent, or Firm* — Andre Roland S.A.; Nikolaus Schibu

(57) ABSTRACT

An orthopedic implant kit comprising a lockable poly-axial screw, a tissue dilatation sleeve, a screw driver, a screw extender, a rod, rod-reduction device, a set screw driver, a torque limiting device and a screw releasing device.

13 Claims, 24 Drawing Sheets

(56) References Cited

U.S. PATENT DOCUMENTS

| | | | |
|---|---|---|---|
| 7,179,225 B2* | 2/2007 | Shluzas | A61B 17/3439 600/219 |
| 7,250,052 B2* | 7/2007 | Landry | A61B 17/1604 606/86 A |
| 7,491,168 B2* | 2/2009 | Raymond | A61B 17/02 600/231 |
| 7,691,129 B2* | 4/2010 | Felix | A61B 17/7037 606/246 |
| 7,842,044 B2* | 11/2010 | Runco | A61B 17/7076 606/104 |
| 7,862,587 B2* | 1/2011 | Jackson | A61B 17/861 606/246 |
| 7,892,238 B2* | 2/2011 | DiPoto | A61B 17/02 606/103 |
| 7,892,259 B2* | 2/2011 | Biedermann | A61B 17/7032 606/246 |
| 7,922,725 B2* | 4/2011 | Darst Rice | A61B 17/7085 606/254 |
| 7,967,821 B2* | 6/2011 | Sicvol | A61B 17/7032 606/264 |
| 8,016,832 B2* | 9/2011 | Vonwiller | A61B 17/7032 606/86 A |
| 8,016,862 B2* | 9/2011 | Felix | A61B 17/7032 606/266 |
| 8,114,085 B2* | 2/2012 | von Jako | A61B 17/02 600/218 |
| 8,128,667 B2* | 3/2012 | Jackson | A61B 17/683 606/273 |
| 8,152,810 B2* | 4/2012 | Jackson | A61B 17/7037 606/104 |
| 8,167,911 B2* | 5/2012 | Shluzas | A61B 17/7037 606/266 |
| 8,246,665 B2* | 8/2012 | Butler | A61B 17/7037 606/251 |
| 8,262,704 B2* | 9/2012 | Matthis | A61B 17/7032 606/264 |
| 8,317,796 B2* | 11/2012 | Stihl | A61B 17/7091 606/279 |
| 8,382,805 B2* | 2/2013 | Wang | A61B 17/8605 606/267 |
| 8,608,746 B2 | 12/2013 | Kolb et al. | |
| 8,636,783 B2* | 1/2014 | Crall | A61B 17/7037 606/272 |
| 9,050,139 B2* | 6/2015 | Jackson | A61B 17/7011 |
| 9,101,401 B2* | 8/2015 | Dalton | A61B 17/7032 |
| 9,138,261 B2* | 9/2015 | Di Lauro | A61B 17/7011 |
| 9,204,909 B2* | 12/2015 | Rezach | A61B 17/7076 |
| 9,211,143 B2* | 12/2015 | Barry | A61B 17/7032 |
| 9,211,149 B2* | 12/2015 | Hoefer | A61B 17/708 |
| 9,408,649 B2* | 8/2016 | Felix | A61B 17/7032 |
| 9,492,209 B2* | 11/2016 | Biedermann | A61B 17/7085 |
| 2006/0089644 A1* | 4/2006 | Felix | A61B 17/7037 606/250 |
| 2006/0111715 A1* | 5/2006 | Jackson | A61B 17/861 128/897 |
| 2007/0270866 A1 | 11/2007 | Von Jako | |
| 2010/0152785 A1* | 6/2010 | Forton | A61B 17/7035 606/301 |
| 2011/0040328 A1 | 2/2011 | Miller et al. | |
| 2011/0172718 A1* | 7/2011 | Felix | A61B 17/7032 606/305 |
| 2011/0263945 A1 | 10/2011 | Peterson | |
| 2011/0313460 A1 | 12/2011 | McLean et al. | |
| 2013/0012999 A1 | 1/2013 | Petit | |
| 2013/0023941 A1* | 1/2013 | Jackson | A61B 17/7005 606/305 |
| 2013/0096624 A1* | 4/2013 | Di Lauro | A61B 17/7011 606/279 |

FOREIGN PATENT DOCUMENTS

| | | |
|---|---|---|
| JP | 2007283101 | 11/2007 |
| JP | 2012507316 | 3/2012 |
| JP | 2013515580 | 5/2013 |
| WO | WO 2010052462 | 5/2010 |
| WO | WO 2011080426 | 7/2011 |

OTHER PUBLICATIONS

First Office Action issued by the China State Intellectual Property Office, dated May 3, 2017, 12 pages.

Office Action dated Feb. 5, 2018 for the State Intellectual Property Office of China (SIPA) for the counterpart application with the Serial No. 201480027310.0.

Japanese Office Action issued by the Japanese Patent Office in the counterpart Japanese Application No. 2016-513463 dated Feb. 6, 2018, 9 pages + English translation.

* cited by examiner

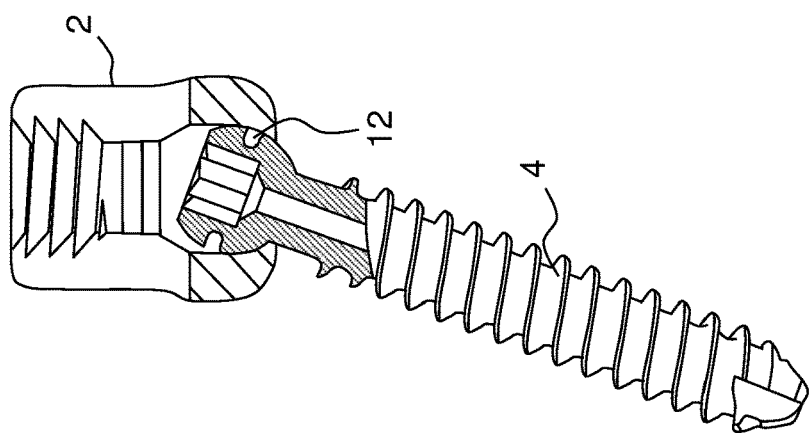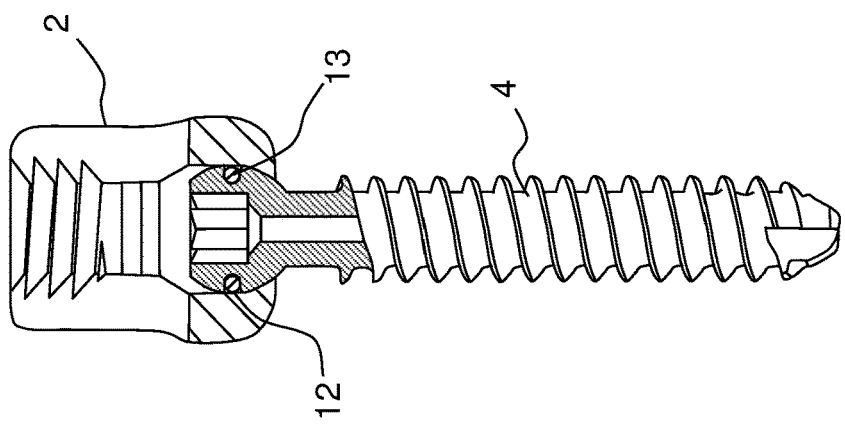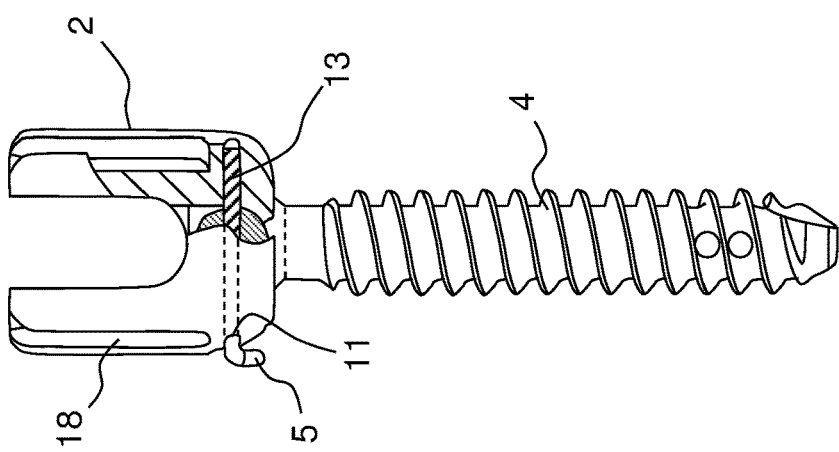

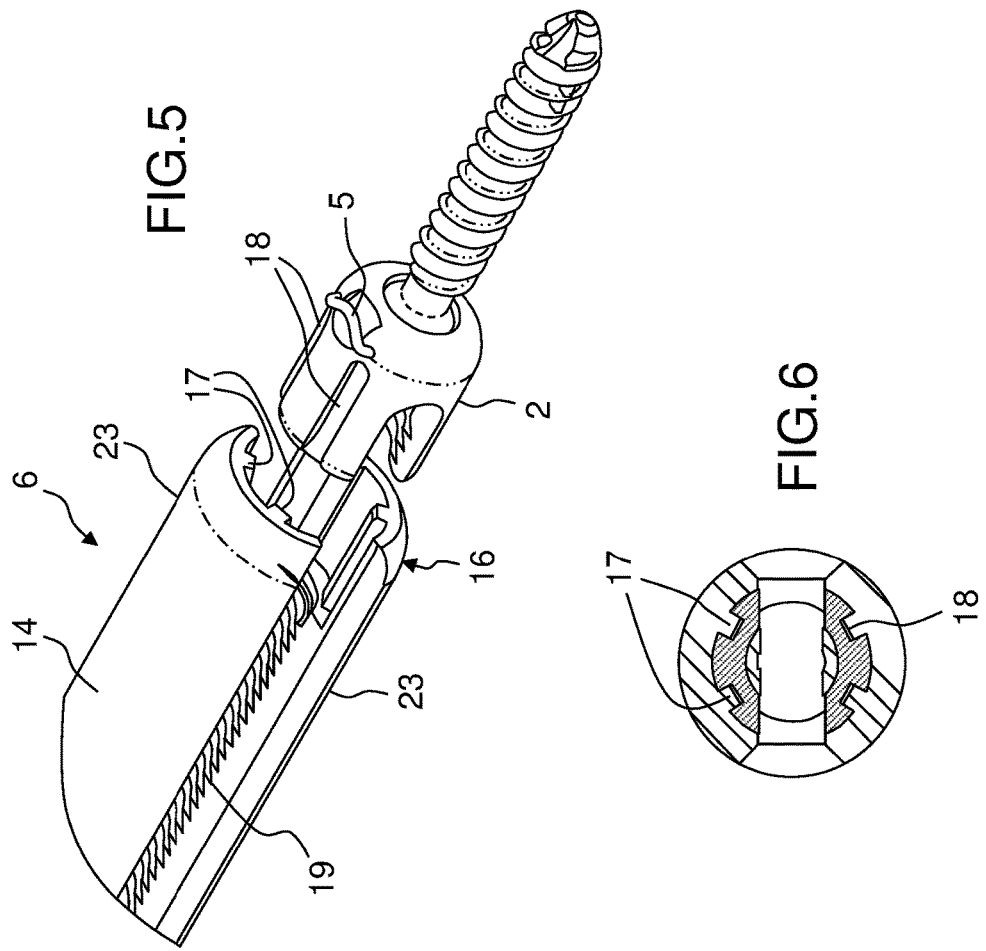
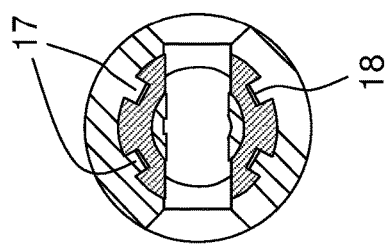
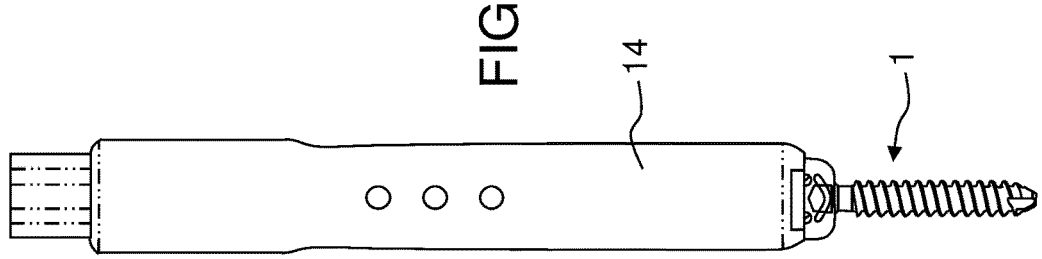

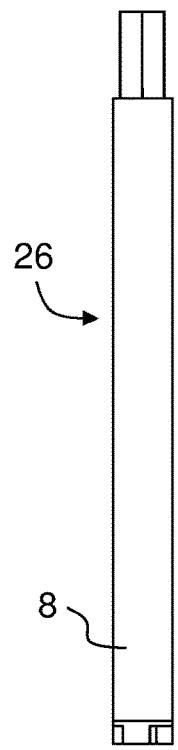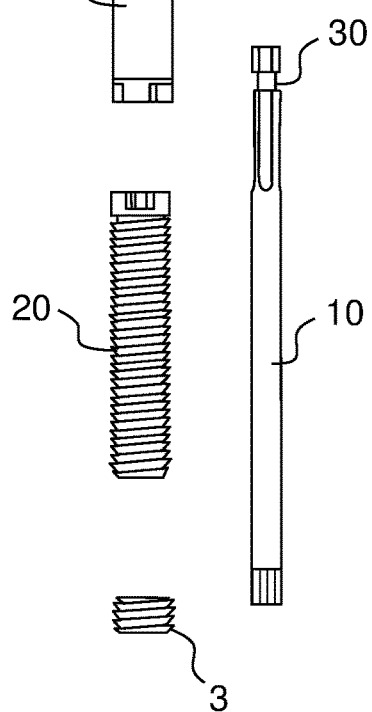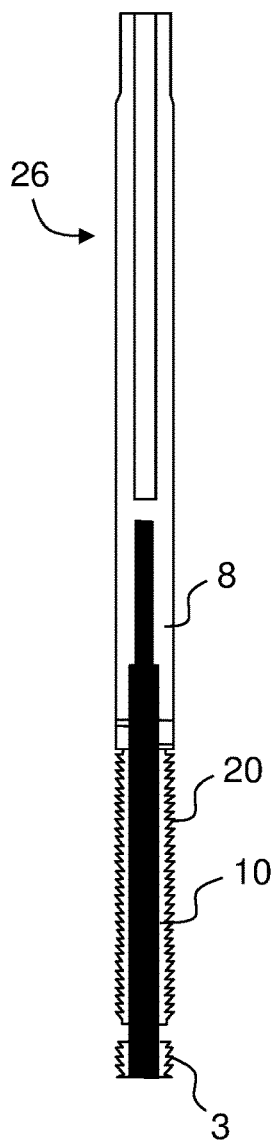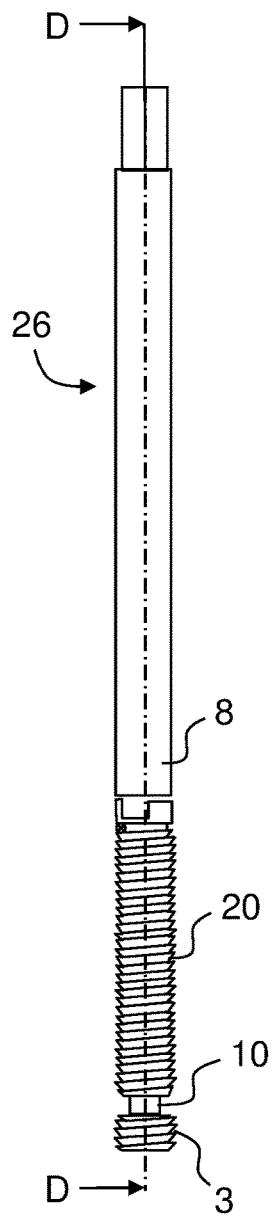
FIG.13A     FIG.13B     FIG.13C

ORTHOPEDIC IMPLANT KIT

This application is the U.S. national stage application of International patent application No. PCT/IB2014/060979, filed on Apr. 24, 2014, which designated the United States, and claims foreign priority to International patent application PCT/IB2013/053892, filed on May 13, 2013, the entire contents of each of which are hereby incorporated by reference.

FIELD OF INVENTION

The present invention relates to orthopedics and more precisely to orthopedic items such as pedicle screws, rods and spine cages. The invention also relates to instruments which are used for manipulating those items.

BACKGROUND

US 2013/0012999 discloses an orthopedic implant kit comprising several items, in particular a pedicle screw fixed to a mounting tube made of two half-shells which can be easily disassembled.

Pedicle screws of the prior art can be divided in two main groups:
Mono-axial screws: The direction of the screw main axis is fixed with respect the screw head;
Poly-axial screws: The orientation of the screw main axis can be freely modified with respect to the screw head.

When implanting a pedicle screw into a bone several steps are needed. For almost each of those steps a dedicated instrument is used.

GENERAL DESCRIPTION OF THE INVENTION

An objective of the present invention is to reduce the number of items which are required for manipulating and fixing an orthopedic implant (pedicle screw, nut, rod, etc. . . . ).

Another objective is to reduce the number of instruments for manipulating those items.

Another objective is to facilitate the handling of the instruments.

Those objectives are met with the implant kit and the related items and instruments which are defined in the claims.

In a first embodiment the invention consists in an orthopedic implant kit comprising a lockable poly-axial screw, a tissue dilatation sleeve, a screw driver, a screw extender, a rod, rod-reduction means, a set screw driver, a torque limiting mechanism and a screw releasing instrument.

The lockable poly-axial orthopedic screw according to the invention comprises a head and a threaded portion which form two separate elements, fixed to each other but each element may be independently oriented along a specific direction. The threaded portion may, for instance, rotates around the screw head and may adopt several possible orientations. More precisely, the threaded portion may be oriented anywhere within a conical volume, the top of the cone corresponding to the contact point between the head and the threaded portion.

The screw furthermore comprises a locking element which, when activated, suppresses the relative movement between the threaded portion and the head. This configuration is named "mono-axial" because the threaded portion may be oriented along a single (fixed) axis with respect to the head.

According one embodiment the locking element is a clip having a U-shape. In this case the head and the threaded portion contains cavities which are adapted to receive the branches of the U-shape clip.

Preferably, in the mono-axial mode the head may still freely rotate around its own axis, with respect to the threaded portion. Such a mechanism may be obtained with a U-shape clip and with an annular groove located around the upper part of the threaded portion. In this case the branches of the clip are sliding within the annular groove.

In another embodiment the screw head contains at least one longitudinal relief, such as a groove or a ridge, which is dimensioned in a way as to receive a corresponding relief, such as a ridge or a groove, which is located within the distal end of a screw extender.

In another embodiment the screw comprises a concave seat located in the proximal end of the threaded portion and a corresponding convex shape located at the distal part of the screw head. This configuration reduces the screw length and increases the strength and the rigidity of the system.

The screw extender according to the invention comprises a hollow cylindrical body made of two half tubes separated by two opposite longitudinal slots having an open end towards the cylindrical body distal part, this later one being dimensioned to receive and hold a screw head. The cylindrical body furthermore comprises an internal threaded part.

According to one embodiment the cylindrical body is made of a single piece and the distal part is radially expandable by its own elasticity, in such a way as to allow an easy clipping and subsequent releasing of a screw head.

To facilitate its radial expansion, the screw extender may include expanding means, for instance an internal rotatable tube which, when rotated pushes away the two half tubes from each other.

In a preferred embodiment the internal part of the cylindrical body distal end contains at least one relief, such as a ridge or a groove, which is dimensioned to be received within the longitudinal relief of a screw head which includes a corresponding relief, as mentioned previously. With this configuration it hinders the distal part of the half tubes to separate from each other by its own elasticity thus making a very strong attachment between the screw extender and the screw head. An additional benefit is that the relative rotation between the screw head and the cylindrical body is avoided.

In a preferred embodiment a rod reduction instrument is located within the cylindrical body. Advantageously the rod reduction instrument is essentially made of a shaft with a threaded distal part which is the counterpart of the cylindrical body internal threaded part. So when it is rotated within the cylindrical body the shaft may move along the cylindrical body main axis.

In another embodiment a set screw driver is (also or alternatively) located within said cylindrical body. In this case also, the set screw driver may also essentially be made of a shaft with a threaded distal part.

Advantageously the set screw driver comprises a torque limiting mechanism.

In one embodiment this mechanism includes a breakable pin and a thread free rotatable shaft. The pin is laterally crossing the rotatable shaft and its ends are fixed within the threaded rotatable shaft. The threaded and the threaded free shafts are rotatably linked to each other but when a certain torque is reached the pin breaks and each shaft may freely rotates with respect to the other shaft.

In another embodiment a screw releasing instrument is (also or alternatively) located within said cylindrical body.

Advantageously the screw releasing instrument is essentially made of a shaft with a threaded distal part.

In a particularly interesting embodiment, the same shaft with a threaded distal part is used for the rod reduction instrument (and potential sponylolisthesis), the set screw driver and the screw releasing mechanism.

The tissue dilatation sleeve according to the invention comprises a flexible conical part which is adapted to be temporarily fixed to the distal part of an instrument such as a screw extender as defined in the previous claims.

In one embodiment the conical part is made of several longitudinal flexible blades having each a substantially triangular shape.

DETAILED DESCRIPTION OF THE INVENTION

The invention will be better understood in the following part of this document, with non-limiting examples illustrated by the following figures:

FIGS. 3A to 3C are cross-sections and partial cut views of the screw of FIG. 2

FIG. 5 shows the distal part of a screw extender according to the invention, together with the screw of FIG. 2

FIG. 6 is a cross section of the screw extender distal part

FIG. 7 is a global view of a screw extender with a screw

FIGS. 13A to 13C show different views of a rotatable shaft which is used in a rod reduction instrument, a set screw driver and a screw releasing instrument

NUMERICAL REFERENCES USED IN THE FIGURES

Figure 1:
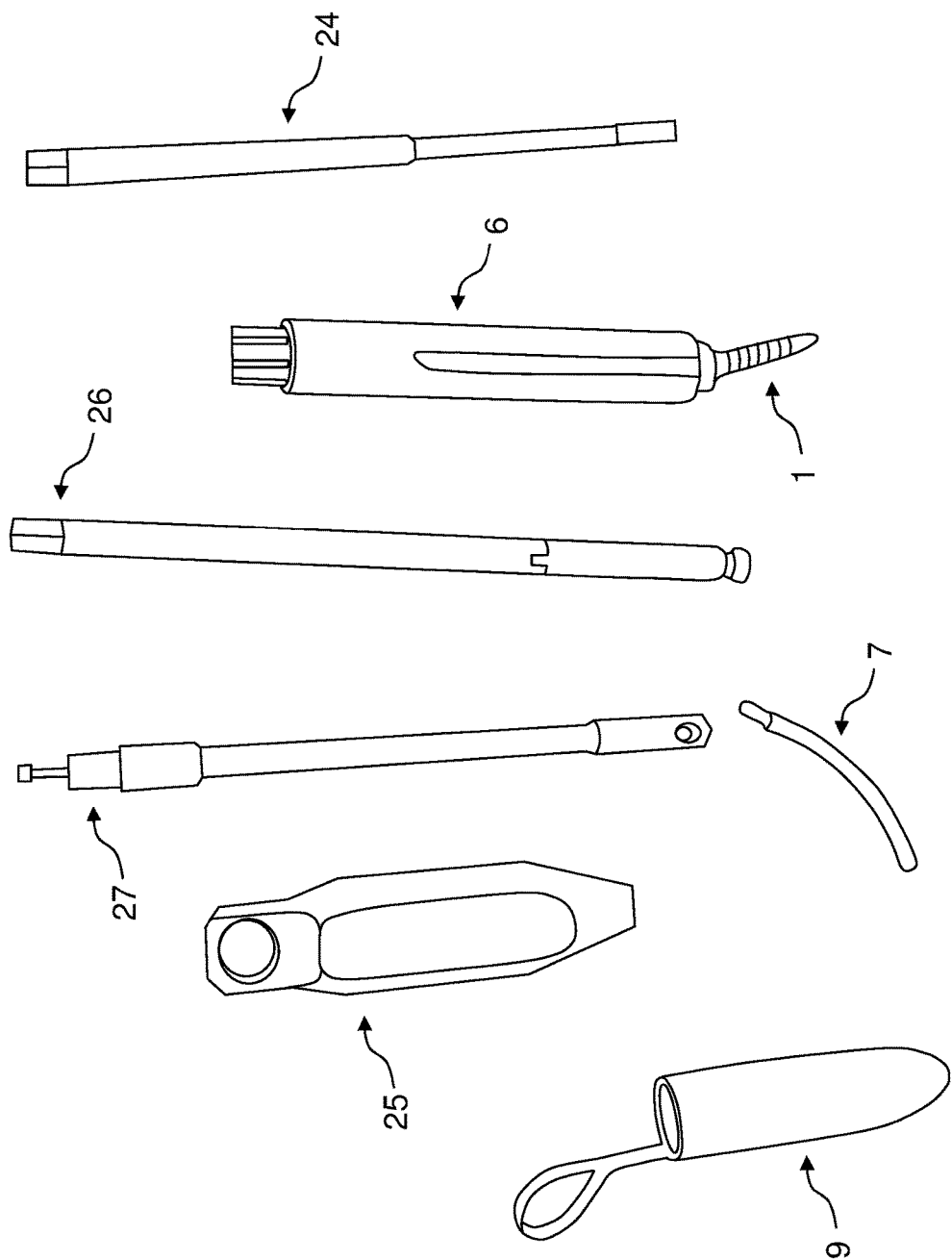
FIG. 1 shows an implant kit according to the invention

1. Pedicle screw
2. Head
3. Set screw
4. Threaded portion
5. Locking element
6. Screw extender
7. Rod
8. Multi-use instrument upper part
9. Tissue dilatation sleeve
10. Torque driver
11. Head passage
12. Threaded portion passage
13. Branch
14. Cylindrical body
15. Slot -continued 16. Cylindrical body distal part
17. Ridge
18. Groove
19. Screw extender internal threaded part
20. Multi-use instrument lower part
21. Conical part
22. Blade
23. Half tube
24. Screw driver
25. Handle
26. Multi-use instrument (Rod reduction/Set screw driver/screw release)
27. Rod inserting instrument
28. Breakable pin
29. Lateral pin
30. Circular groove
31. Puncturing needle/Guide wire
32. Concave screw top
33. Convex upper half ball The examples below more precisely relate to a thoracolumbar fusion system consisting of pedicle screws and rods combined with single use instruments. A typical pedicle screw system consists of the screw implants and the instruments for placing the screws.

FIG. 1 shows an example of an implant kit according to the invention.

This kit contains a tissue dilatation sleeve 9, a handle 25, a rod 7, a rod inserting instrument 27, a shaft 26 which can be used as a rod reduction instrument and/or a set screw driver and/or a screw releasing instrument, a pedicle screw 1, a screw extender 6 and a screw driver 24.

Figure 2:
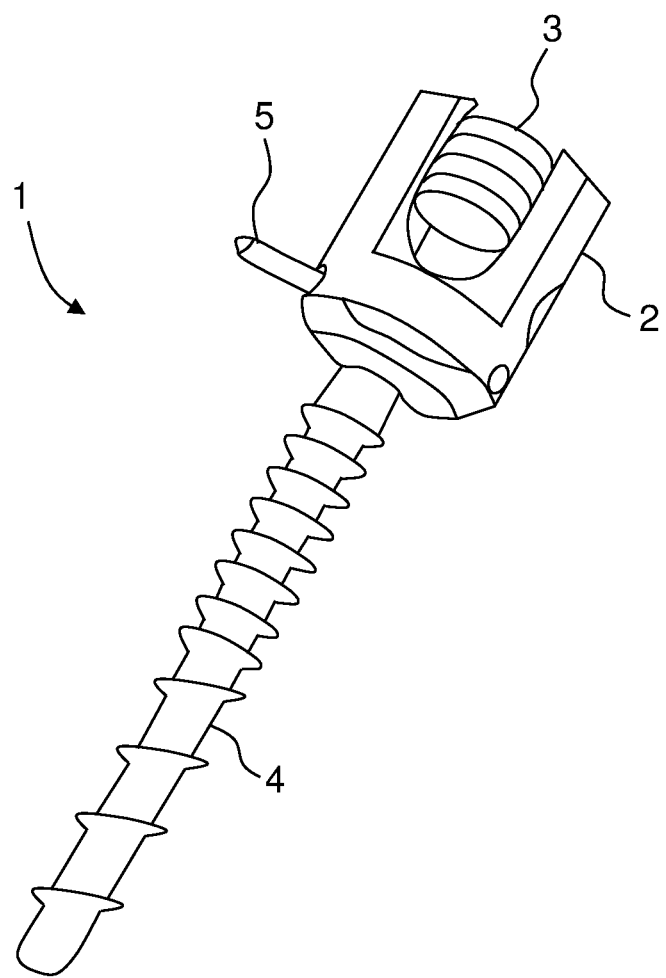
FIG. 2 shows an example of a lockable poly-axial pedicle screw according to the invention
Figure 4:
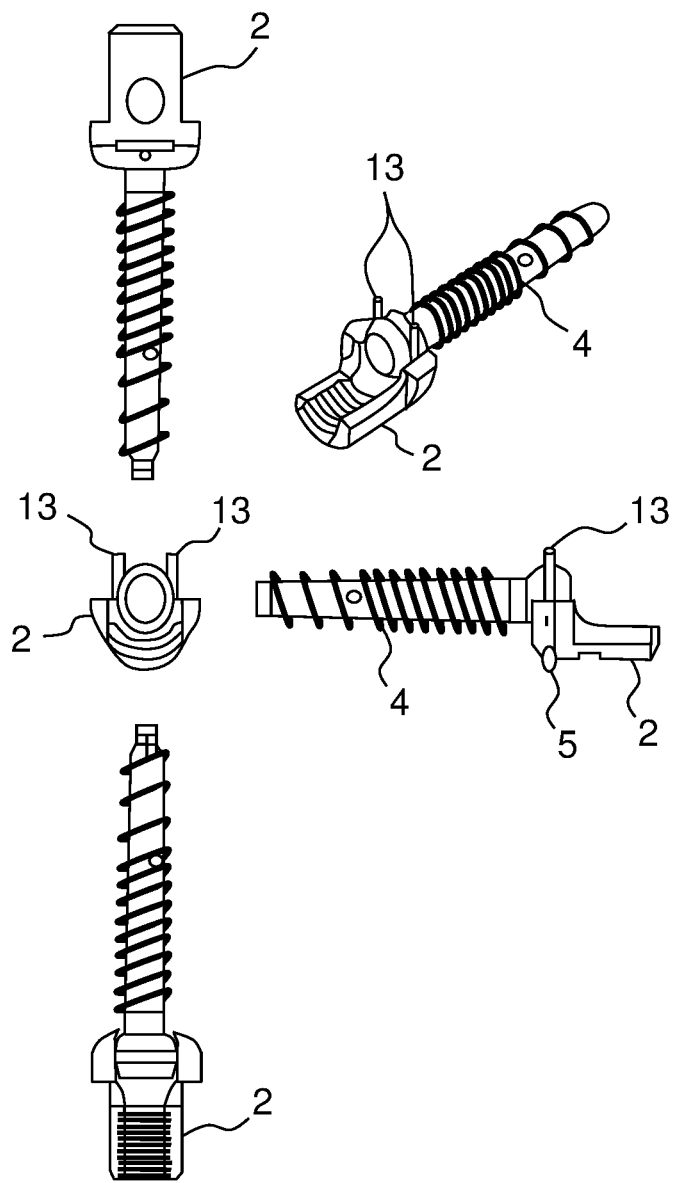
FIG. 4 represents different views (complete and partial) of the screw of FIG. 2

The lockable poly-axial screw 1 illustrated in particular in FIGS. 2 to 4 includes a head 2 and a threaded portion 4. FIG. 2 also shows a set screw 3 which may be fixed to the head after the insertion of a rod 7. The screw 1 furthermore comprises a locking element 5 having a U-shape. When the locking element 5 is fully inserted in the screw head 2 the orientation of threaded portion 4 is blocked with respect to the head 2. Inversely, when the locking element is retrieved, the threaded portion 4 can be freely oriented with respect to the screw head 2.

The lockable poly-axial screw according to the invention may therefore be transformed into a mono-axial screw, thus allowing having mono-axial and poly-axial capability in the same product. A blocking system defined previously allows the surgeon to choose if he/she wants to use the screw in mono-axial or poly-axial mode. As mentioned mono-axial capability is achieved by pushing the locking element (clip) 5 and poly-axial capability is achieved by removing the clip 5. The clip 5 is just an example of a blocking system; other technical solutions can also be imagined such as a pin.

Preferably, in the mono-axial mode the head may still freely rotate around its own axis, with respect to the threaded portion. Such a mechanism may be obtained with a U-shape clip and with an annular groove located around the upper part of the threaded portion. In this case the branches of the clip are sliding within the annular groove.

Any orientation of the axis can be considered when the mono-axial is used, i.e. the screw axis and the screw head may be oriented along different directions.

FIGS. 5 to 7 represent the attachment of a pedicle screw 1 to the distal end 16 of a screw extender 6, by inserting the screw head 2 within the distal end 16. In this operation the head 2 is guided with a plurality of ridges 17 located within the distal end 16 and grooves located on the head 2. With such a system the screw head is better retained within the screw extender 6.

Any suitable material can be used for the screw extender 6 (plastic, polymer, metal, etc. . . . ).

Figures 8A, 8B, 8C:
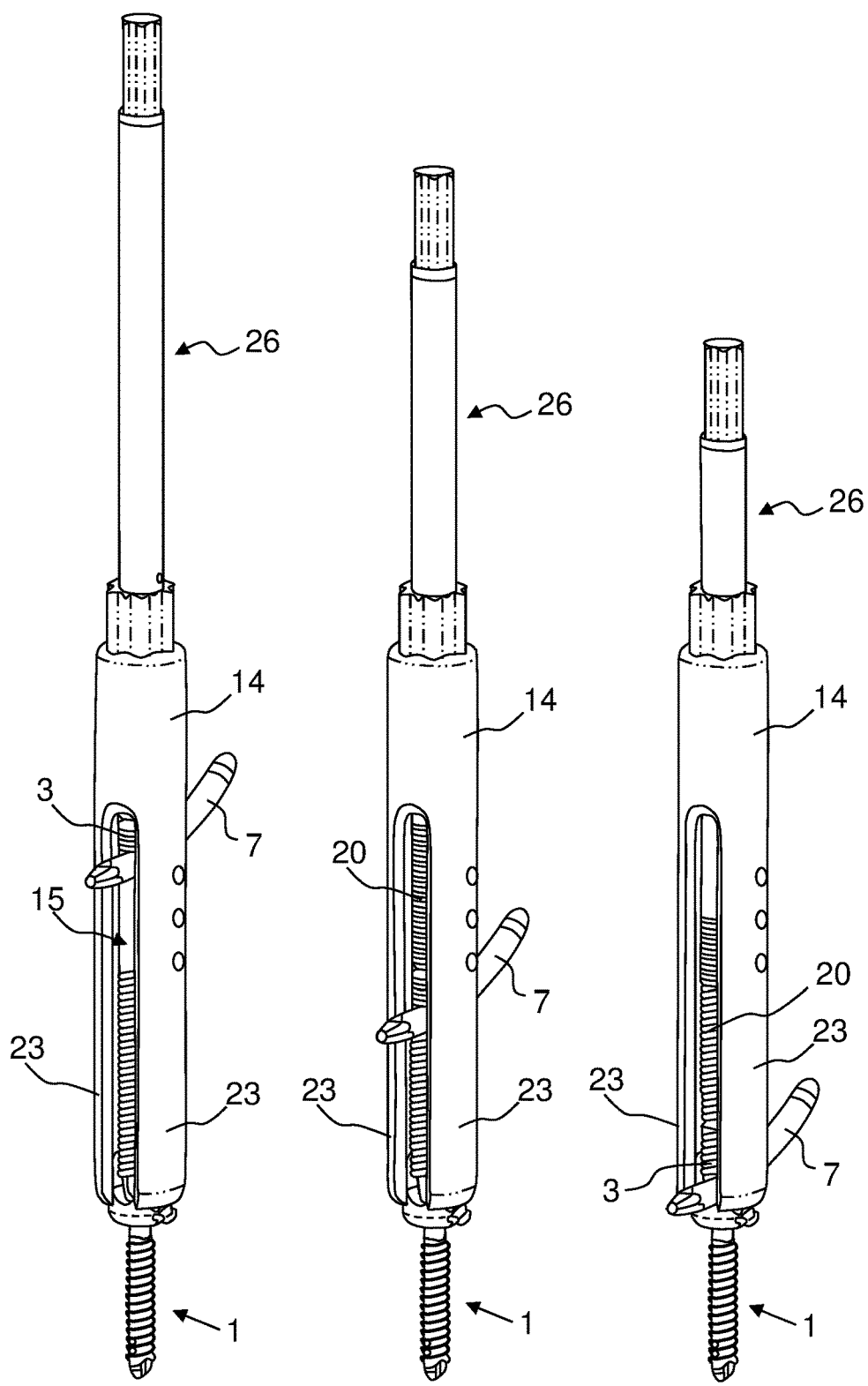
FIGS. 8A to 8C represent the positioning of the rod in the screw head, rod reduction and the tightening of the set screw

FIGS. 8A to 8C represent the positioning of the rod 7 in the screw head 2, a rod reduction and the tightening of the set screw 3 in the screw head 2.

The multi-use instrument 26 (see also FIGS. 13A to 13B) is defined by an upper part 8 and a lower (threaded) part 20.

The rod 7 may be pushed downwards by rotating the multi-use instrument 26 within the cylindrical body 14.

After the rod insertion within the head 2, the set screw 3 is fixed to the head 2 by further rotating the multi-use instrument 26.

Figure 9A:
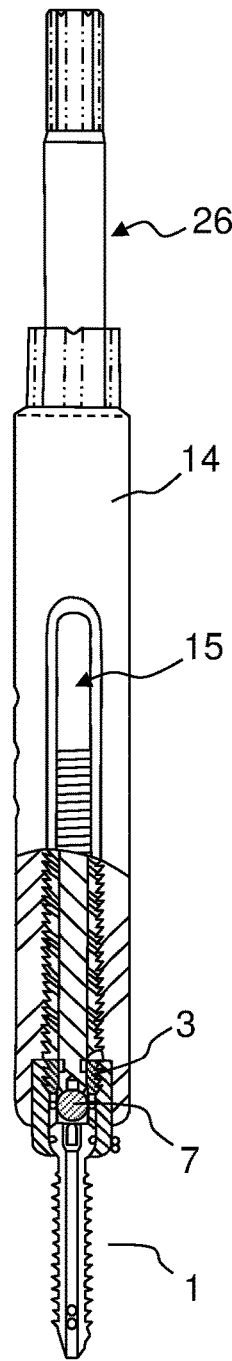
FIGS. 9A to 9C illustrate the release of the screw with respect to the screw extender
Figure 9B:
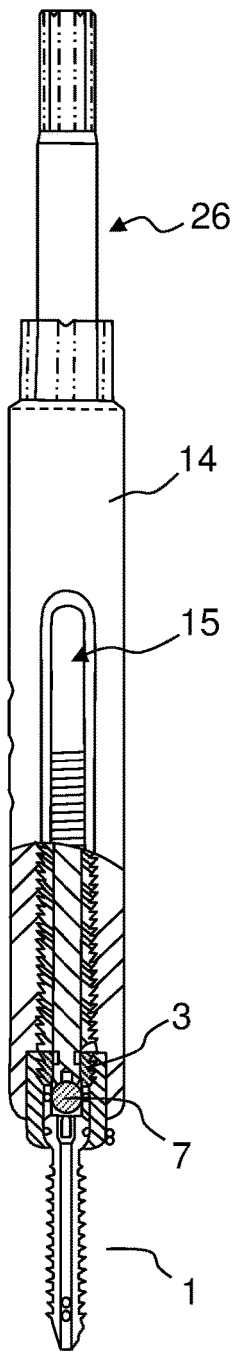
Figure 9C:
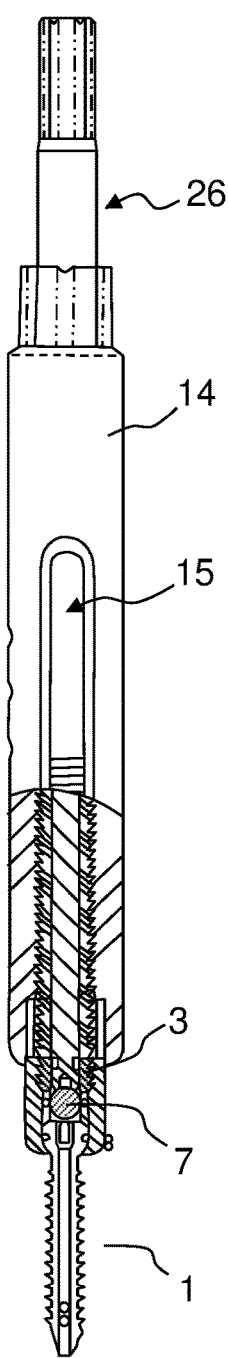
Figure 14:
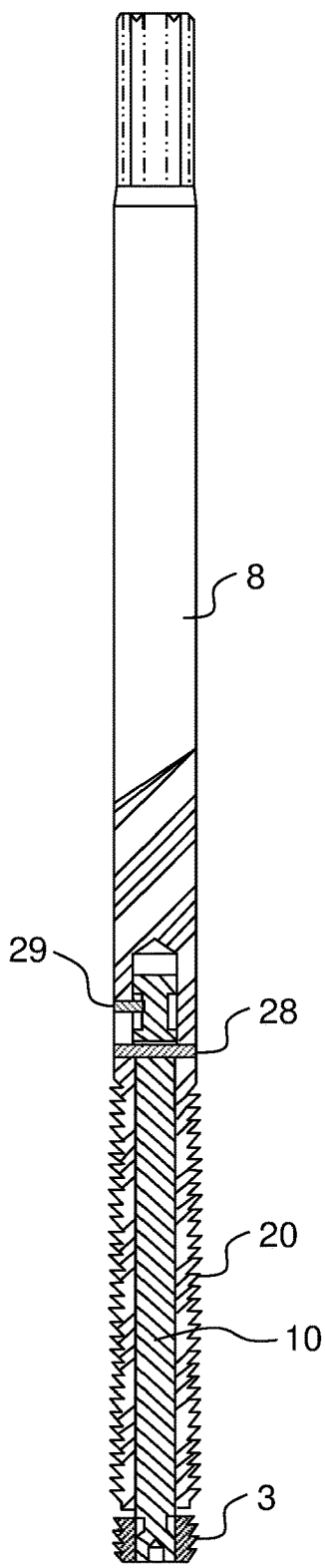
FIGS. 14 and 15 illustrate a torque limiting mechanism
Figure 15:
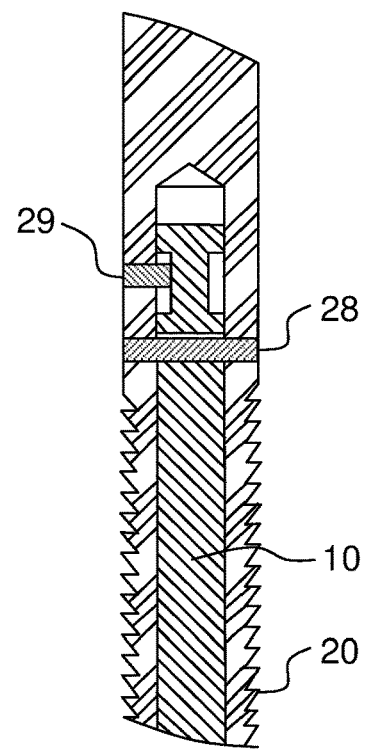

The multi-use instrument 26 is also provided with a torque limiting mechanism (see FIGS. 14 and 15). When the set screw 3 is fixed within the head 2 and the multi-use instrument 26 further rotated, the torque increases, up to a point where the pin 28 breaks. A further rotation of the multi-use instrument 26 has therefore no more effect on the set screw 3. From that point the further rotation of the multi-use instrument 26 only induces a downwards pressure on the screw head 2. The screw 1 is therefore progressively separated from the screw extender (see FIGS. 9A to 9C).

This screw releasing mechanism from an instrument offers the possibility to release the screw 1 from the screw extender without laterally expanding the screw extender 6.

It should be mentioned at this stage that this mechanism is not limited to the release of pedicle screws. Any other item may be used.

To summarize, the same instrument 26 can be used for rod reduction, for fixing a set screw to a screw head and for releasing a screw from a screw extender.

It should be underlined that the invention is not limited to this triple use of the same instrument. A double use is also comprised, for instance rod-reduction and fixation of the screw set to the screw head.

Figure 10:
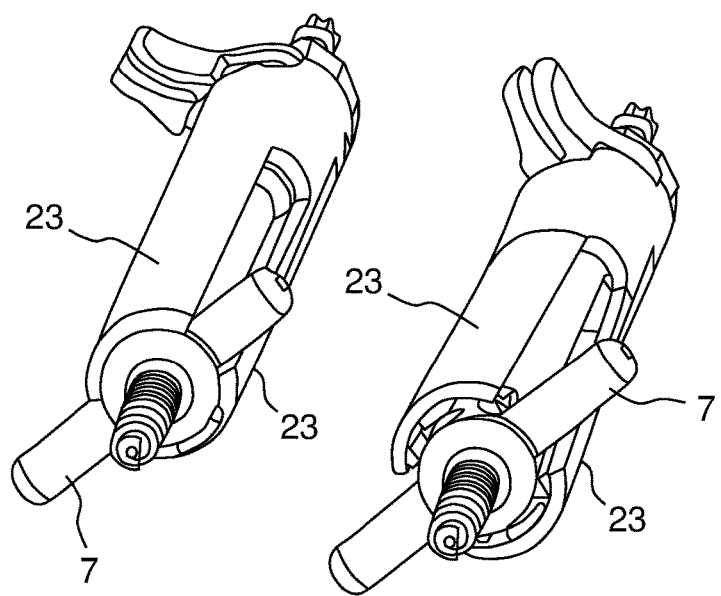
FIG. 10 shows a screw extender which includes a mechanism for laterally expanding the screw extender distal part
Figure 11:
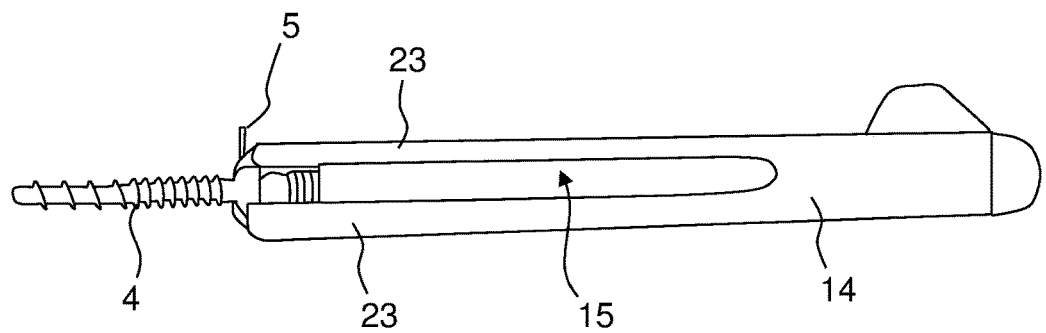
FIG. 11 is another representation of the screw extender of FIG. 10

FIGS. 10 and 11 show an alternative solution to attach a pedicle screw to an screw extender, by rotating an inside tube (not illustrated) the half-tubes 23 are expanded by their own elasticity. This allows a screw to be inserted and fixed to it by for example clamping the outer surface around the screw. The same principle can be used as an alternative to detach the screw extender from a screw. The clamping system also achieves part of its rigidity, by resting on support surfaces on the screw head.

Figure 12:
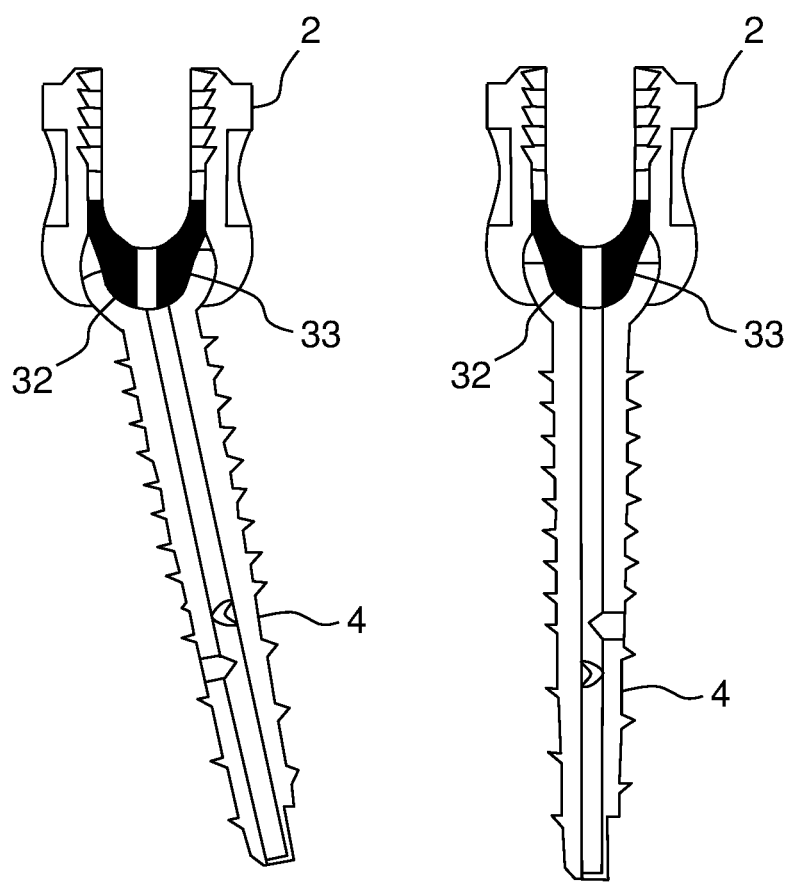
FIG. 12 shows another embodiment of a pedicle screw according to the invention

FIG. 12 shows a concave screw top 32, inside a convex upper half ball 33, allowing the rod 7 and the set screw 3 to be set lower in the screw head 2, thus decreasing the total build height, and increasing the strength and rigidity of the system.

Figure 16:
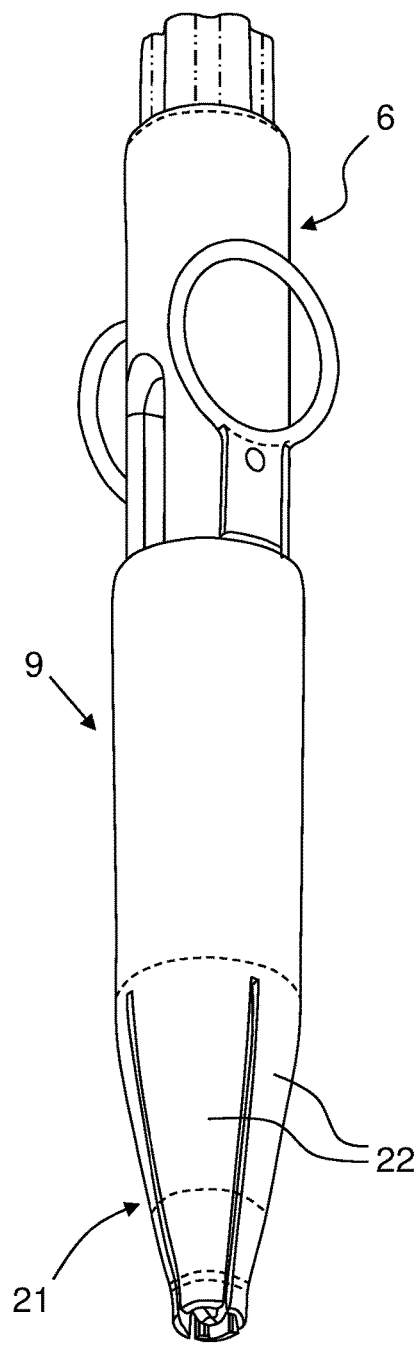
FIGS. 16 and 17 show the use of a tissue dilatation sleeve
Figure 17:
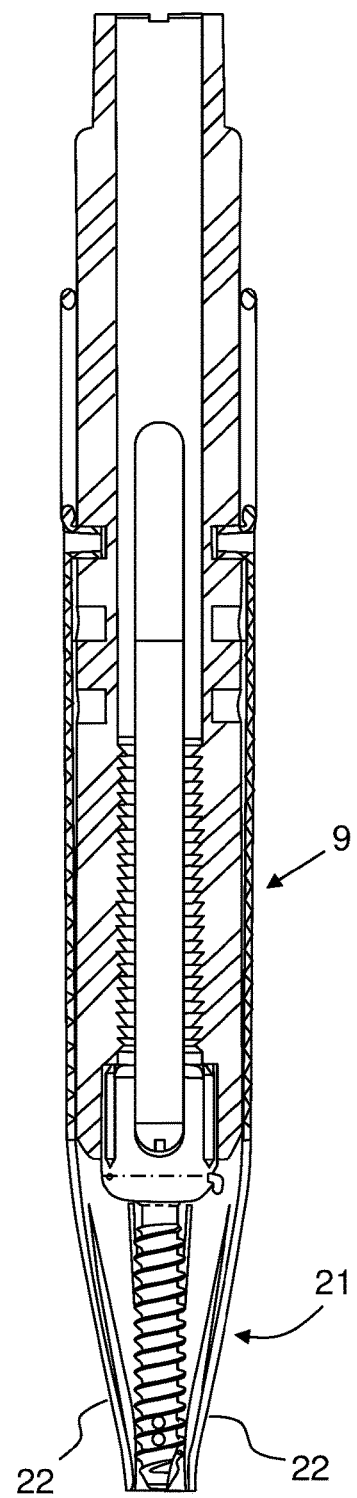
Figure 19:
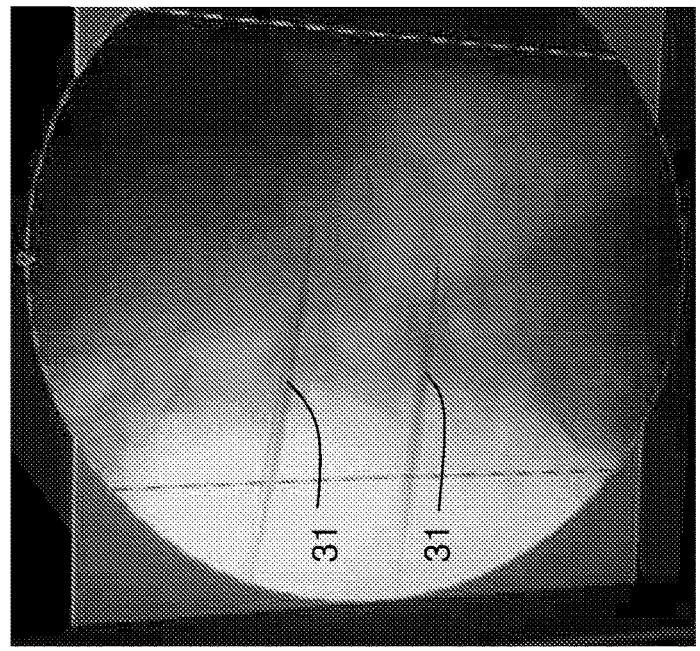
FIGS. 18 to 38 show a procedure using an implant kit according to the invention
Figure 18:
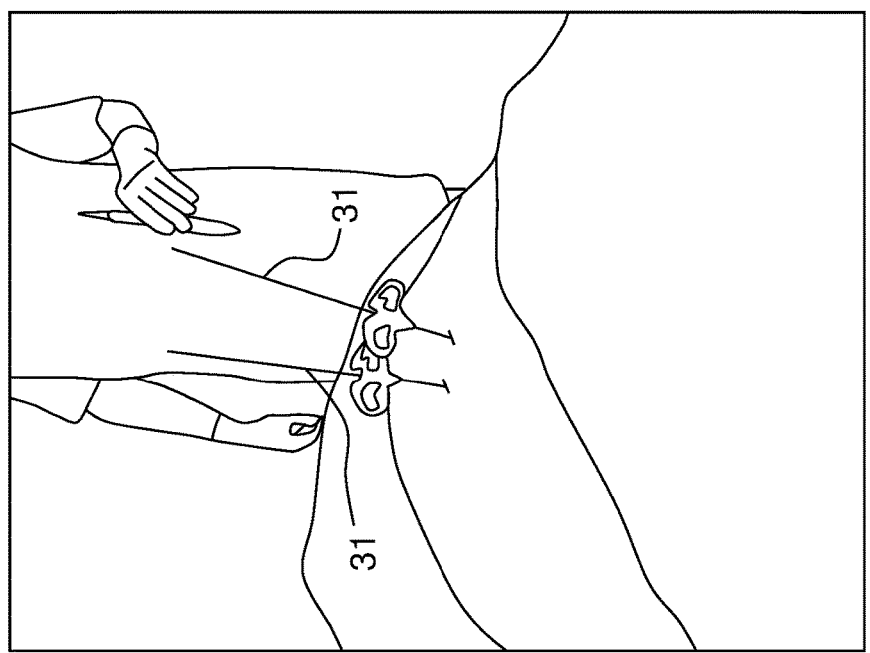
Figure 21:
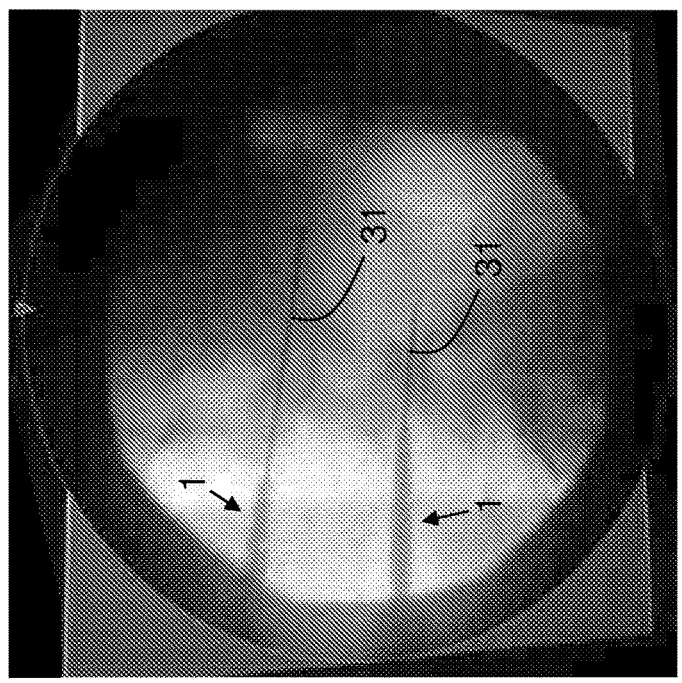
Figure 20:
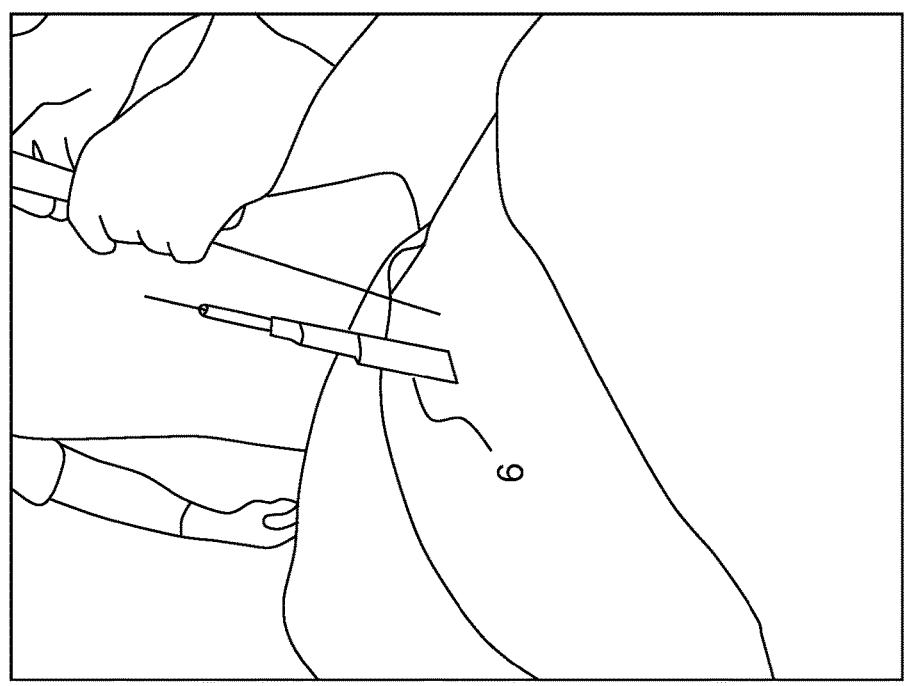

FIGS. 16 and 17 represents a tissue dilatation sleeve 9 containing four triangular flexible blades 22 intervened into each other and forming a cone 21. The cone 21 is mounted at the tip of a screw extender 6, with a tear off spiral. This allows the tissue to be pushed aside as the screw extender 6 is inserted into a body. Once in place, the surgeon may remove the sleeve 9 while the screw extender remains in the body. Any suitable number of blades can be used for forming the cone.

FIGS. 18 to 38 show a procedure using the items which have been previously presented.

In a first step (FIGS. 18 and 19) two puncturing guide wires 31 are positioned in the spine.

A first screw extender 6 with a screw 1 attached and surrounded by a dilatation sleeve is then inserted through the tissue (FIGS. 20 and 21), and along the guide wire 31. The screw extender 6 is rotated and/or pushed.

Figure 23:
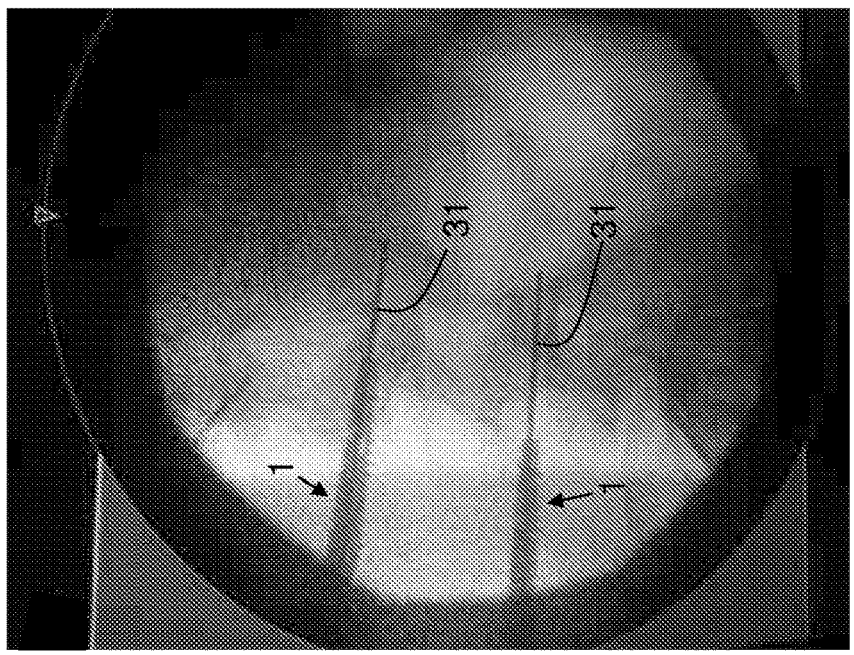
Figure 22:
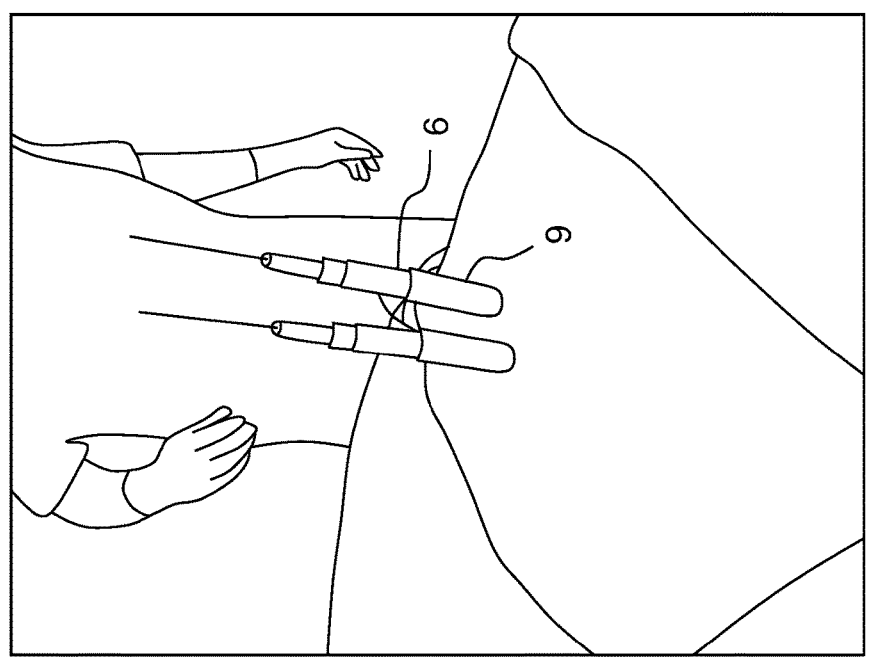

A similar operation is carried out with a second screw extender 6 and screw 1 (FIGS. 22 and 23).

Figure 25:
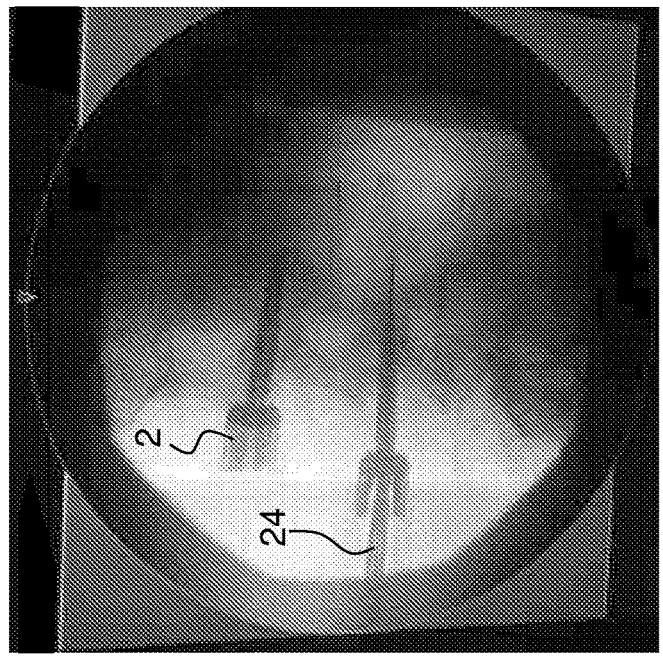
Figure 24:
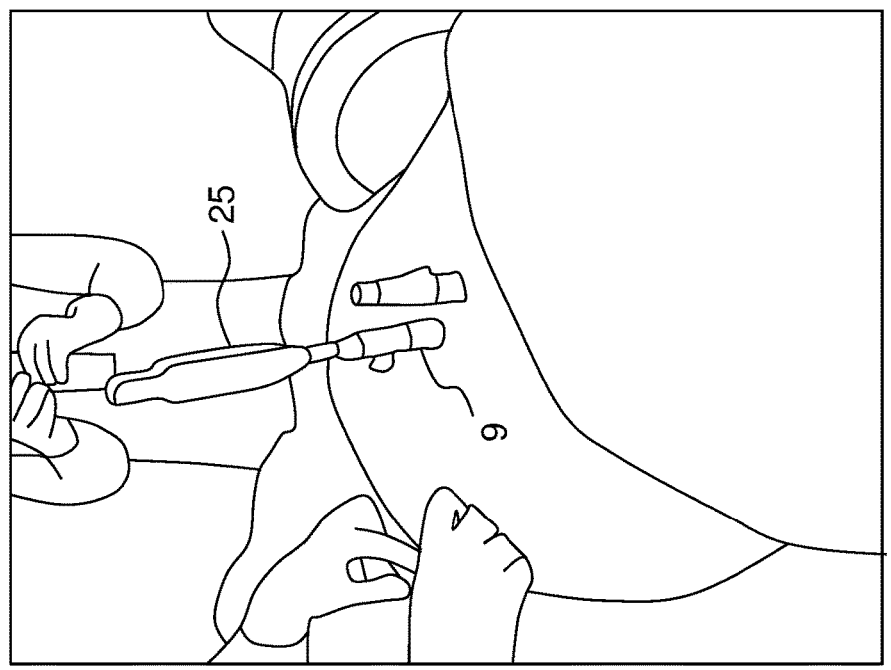

A screw driver 24 is inserted within the screw extender 6. Its distal end is introduced within the upper part of the screw threaded portion 4. The screws 1 are then rotated and enter the vertebrae (FIGS. 24 and 25).

Figure 27:
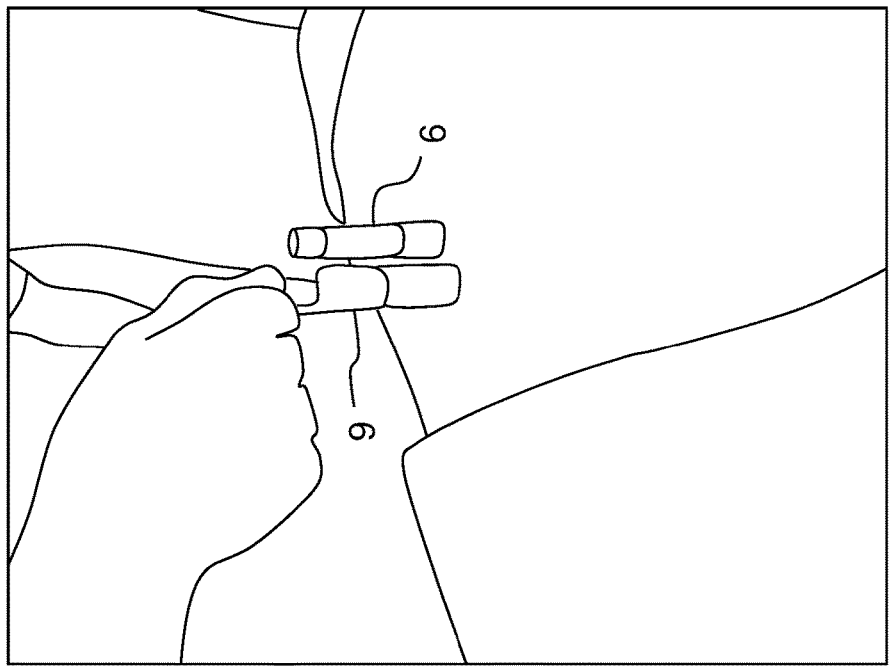
Figure 26:
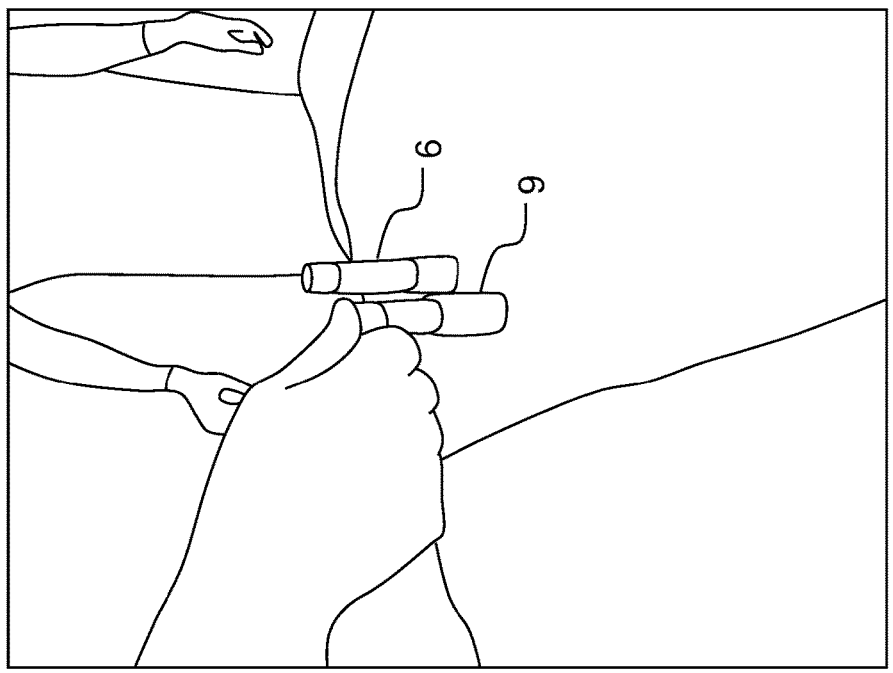
Figure 28:
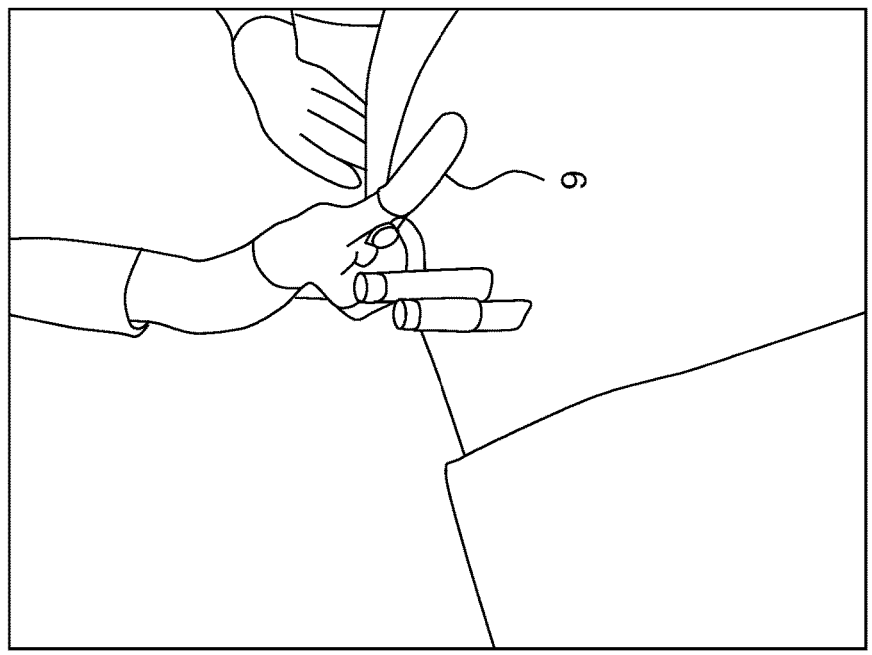

The tissue dilatation sleeves 9 are removed (FIGS. 26 to 28).

Figure 30:
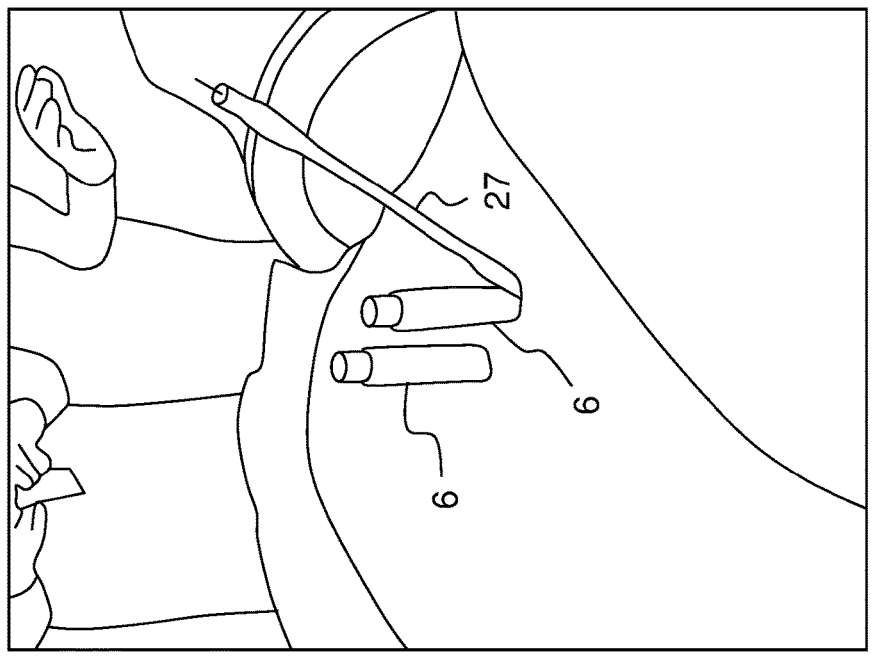
Figure 29:
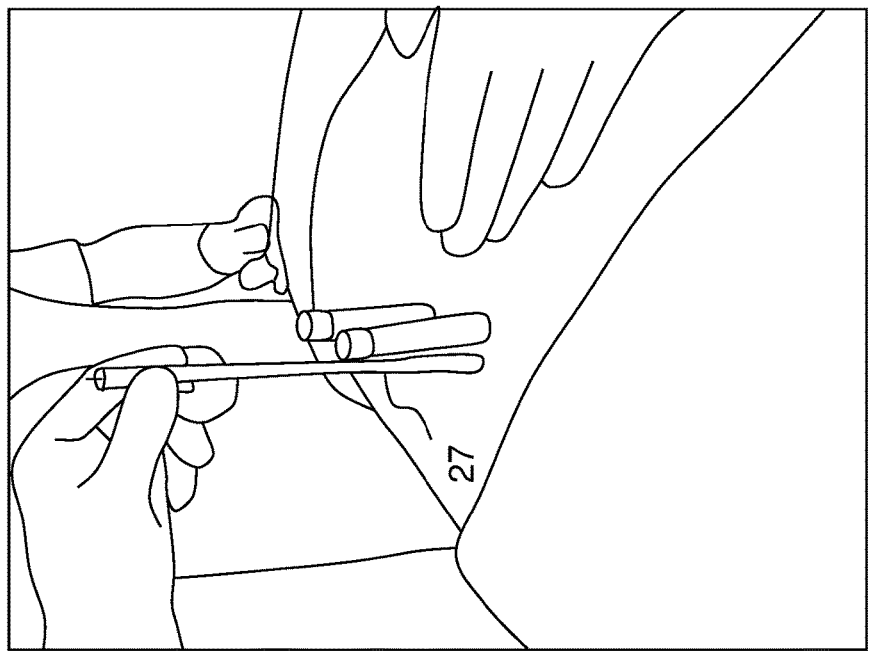

A rod inserting instrument 27 with a rod 7 at its end is transversally crossing the tissue (FIGS. 29 and 30).

Figure 32:
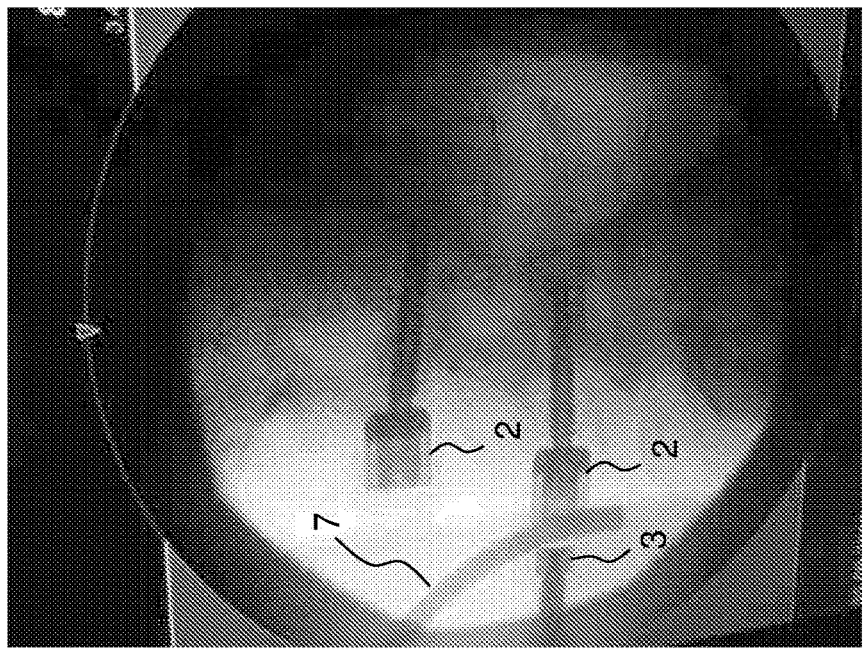
Figure 31:
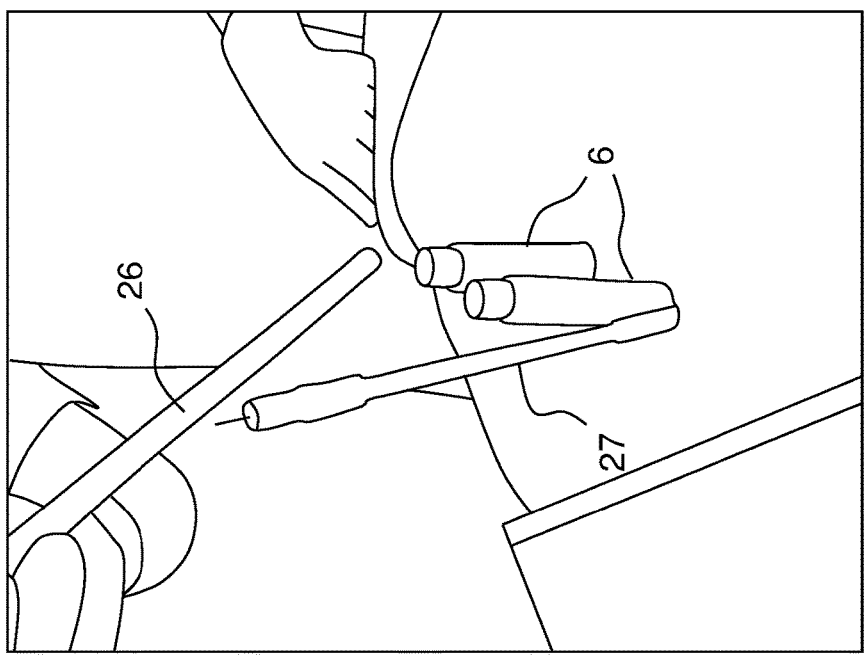
Figure 34:
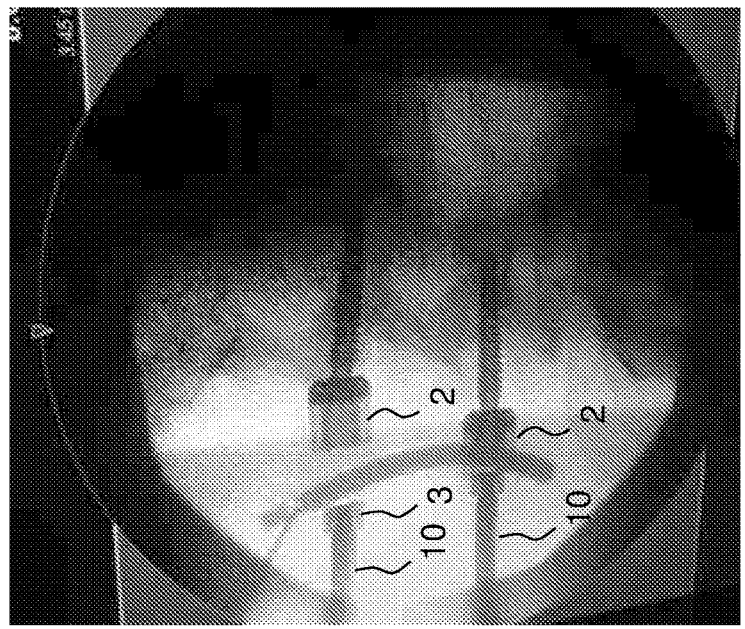
Figure 33:
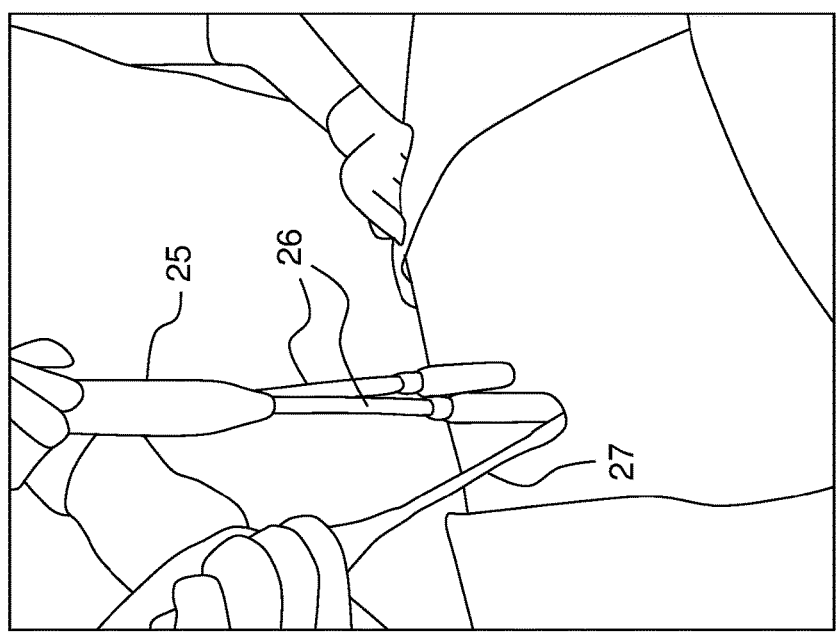
Figure 36:
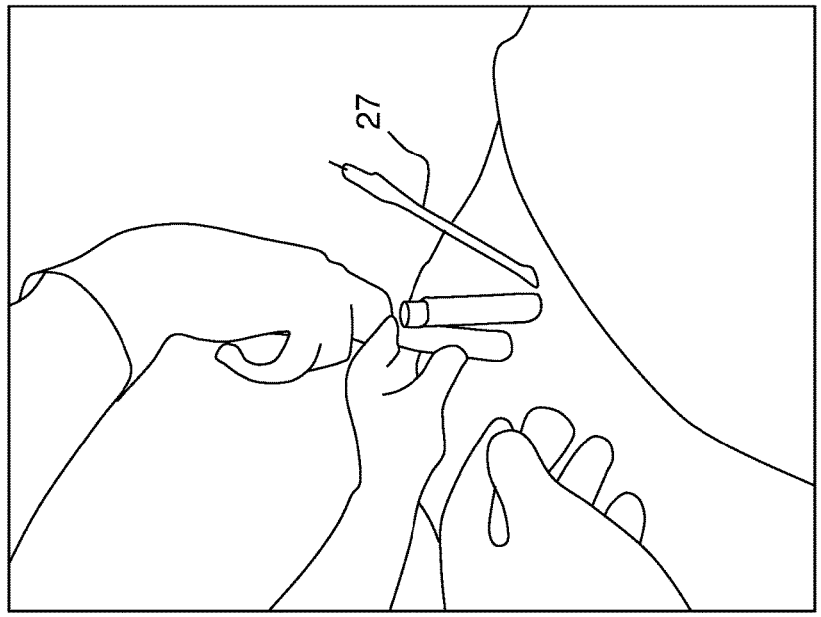
Figure 35:
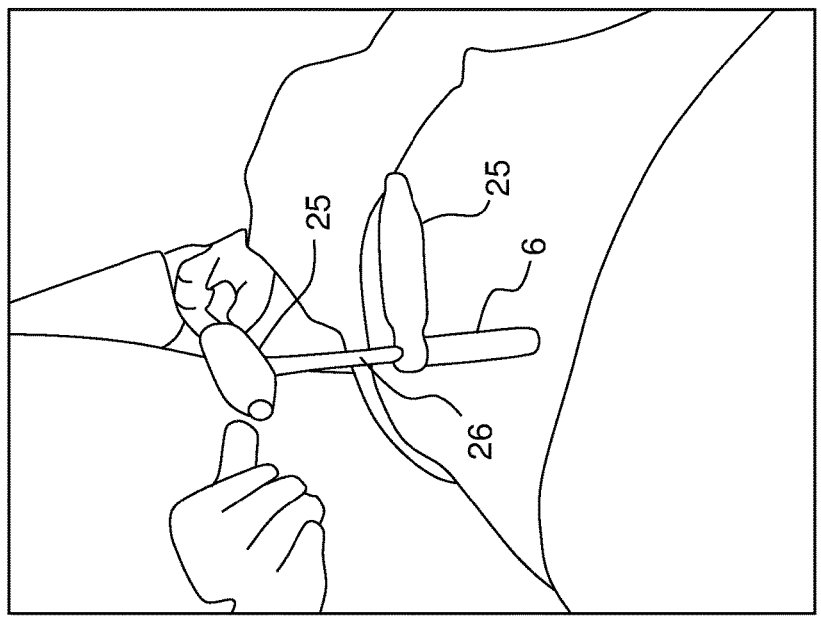

The rod 7 is positioned above the screw head 2 (FIG. 32) and the multi-use instrument 26 is introduced within the screw extender 6, to such an extent that the set screw 3 is positioned above the rod 7, in line with the screw head 2 (FIGS. 31 and 32).

FIGS. 33 to 36 show the rod placement within the screw heads 2 and the fixation of the set screw 3 within the screw head 2.

Figure 38:
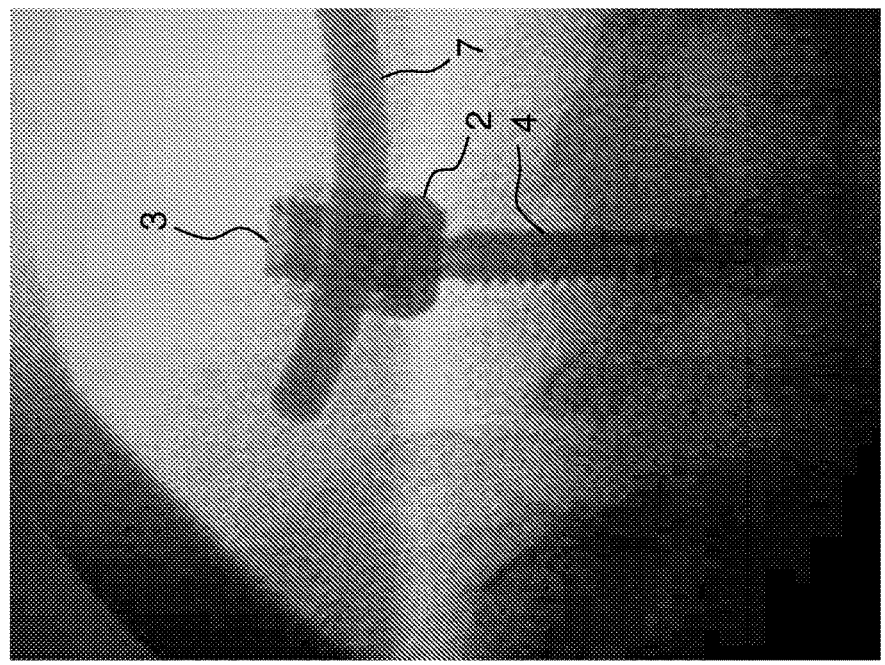
Figure 37:
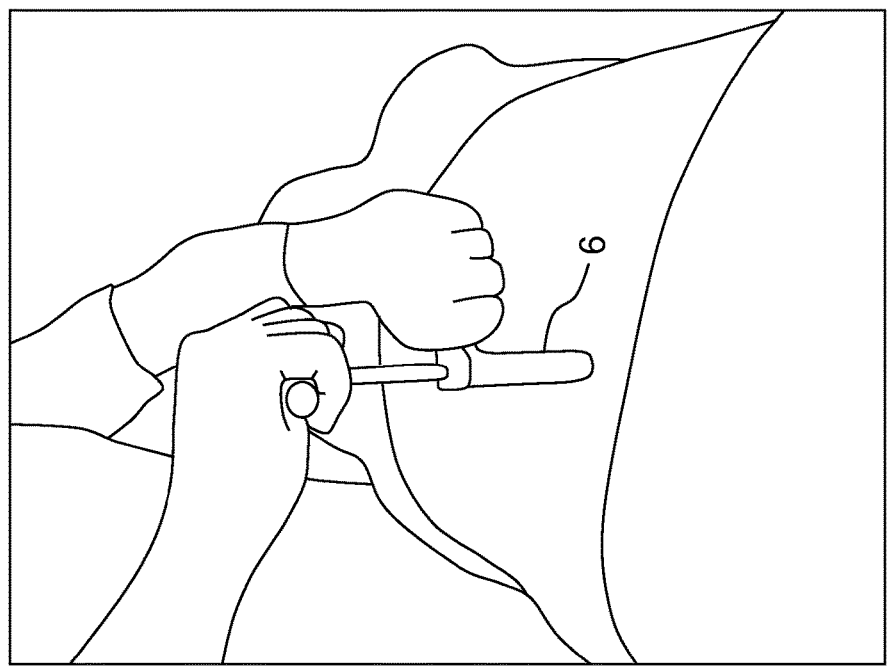

FIGS. 37 and 38 illustrate the screw release from the screw extender 6 and the screw 1, the rod 7 and the screw set 3 in their definitive location.

The invention is of course not limited to those illustrated examples.

The screw extender according to the invention may be used with mono-axial, poly-axial or lockable poly-axial screws.

The invention claimed is:

1. An implant kit comprising:
   a screw extender including,
      a hollow cylindrical body including two opposite longitudinal slots having an open end towards a distal part of the hollow cylindrical body, the distal part configured to receive a screw by an insertion in a direction of a main axis of the hollow cylindrical body, the hollow cylindrical body including an internal thread;
   a multi-use instrument having an external thread configured to threadably engage with the internal thread inside the hollow cylindrical body of the screw extender, the multi-use instrument including,
      a longitudinal outer shell;
      a rotatable shaft located inside the longitudinal outer shell, the rotatable shaft having a distal portion configured to engage with the screw; and
      a blocking mechanism configured to block a rotation of the rotatable shaft relative to the longitudinal outer shell in a blocked position and configured to allow the rotation of the rotatable shaft relative to the longitudinal outer shell in an unblocked position.

2. The implant kit according to claim 1, wherein the blocking mechanism is configured as a torque limiting device engaging with the longitudinal outer shell and the rotatable shaft.

3. The implant kit according to claim 1, wherein the blocking mechanism includes a breakable pin that laterally crosses at least a portion of the longitudinal outer shell and the rotatable shaft.

4. The implant kit according to claim 2, wherein the torque limiting device is configured to block the rotation of the rotatable shaft relative to the longitudinal outer shell in the blocked position, and upon reaching a certain torque, the torque limiting device is configured to allow the rotation of the rotatable shaft relative to the longitudinal outer shell in the unblocked position.

5. The implant kit according to claim 1, wherein in the blocked position, the multi-use instrument together with the screw extender is configured as a screw driver to turn the screw relative to the screw extender by engagement via the distal portion of the rotatable shaft, and in the unblocked position, the multi-use instrument together with the screw extender is configured as a screw releasing device to push the screw away from the distal part of the screw extender in the direction of the main axis of the hollow cylindrical body of the screw extender, to release the screw.

6. The implant kit according to claim 1, further comprising:
a set screw configured to removably engage with the distal portion of the rotatable shaft, the set screw having an external thread; and
a pedicle screw configured to removably engage with the distal part of the hollow cylindrical body of the screw extender, the pedicle screw having a threaded portion and a screw head, the screw head having an internal thread,
wherein the distal portion of the rotatable shaft is configured to engage with the set screw, and upon rotation of the multi-use instrument, the set screw is threadably rotated with the internal thread of the hollow cylindrical body of the screw extender into the internal thread of the screw head such that the multi-use instrument operates as a set screw driver.

7. The implant kit according to claim 6, wherein the two opposite longitudinal slots of the hollow cylindrical body are configured for insertion of a rod between the set screw and the pedicle screw, such that the implant kit operates as a rod reduction device.

8. An implant kit comprising:
a screw extender including,
a hollow cylindrical body including two opposite longitudinal slots having an open end towards a distal part of the hollow cylindrical body, the distal part configured to receive a screw by an insertion in a direction of a main axis of the hollow cylindrical body, the hollow cylindrical body including an internal thread;
a multi-use instrument having an external thread configured to threadably engage with the internal thread inside the hollow cylindrical body of the screw extender, the multi-use instrument including,
a longitudinal outer shell;
a rotatable shaft located inside the longitudinal outer shell, the rotatable shaft having a distal portion configured to engage with the screw; and
a torque limiting device engaging with the longitudinal outer shell and the rotatable shaft,
wherein the torque limiting device is configured to block a rotation of the rotatable shaft relative to the longitudinal outer shell in a blocked position, and upon reaching a certain torque, the torque limiting device is configured to allow the rotation of the rotatable shaft relative to the longitudinal outer shell in an unblocked position.

9. The implant kit according to claim 8, wherein the torque limiting device includes a breakable pin that laterally crosses at least a portion of the longitudinal outer shell and the rotatable shaft.

10. The implant kit according to claim 8, wherein in the blocked position, the multi-use instrument together with the screw extender is configured as a screw driver to turn the screw relative to the screw extender by engagement via the distal portion of the rotatable shaft up to the certain torque, and in the unblocked position, the multi-use instrument together with the screw extender is configured as a screw releasing device to push the screw away from the distal part of the screw extender in the direction of the main axis of the hollow cylindrical body of the screw extender, to release the screw.

11. The implant kit according to claim 8, further comprising:
a set screw configured to removably engage with the distal portion of the rotatable shaft, the set screw having an external thread; and
a pedicle screw configured to removably engage with the distal part of the hollow cylindrical body of the screw extender, the pedicle screw having a threaded portion and a screw head, the screw head having an internal thread,
wherein the distal portion of the rotatable shaft is configured to engage with the set screw, and upon rotation of the multi-use instrument, the set screw is threadably rotated with the internal thread of the hollow cylindrical body of the screw extender into the internal thread of the screw head such that the multi-use instrument operates as a set screw driver.

12. The implant kit according to claim 11, wherein the two opposite longitudinal slots of the hollow cylindrical body are configured for insertion of a rod between the set screw and the pedicle screw, such that the implant kit operates as a rod reduction device.

13. The implant kit according to claim 8, wherein in the blocked position, the multi-use instrument together with the screw extender is configured as a screw driver to turn the screw relative to the screw extender by engagement via the distal portion of the rotatable shaft, and in the unblocked position, the multi-use instrument together with the screw extender is configured as a screw releasing device to push the screw away from the distal part of the screw extender in the direction of the main axis of the hollow cylindrical body of the screw extender, to release the screw from the screw extender.

* * * * *